United States Patent [19]

Rubinstein et al.

[11] Patent Number: 5,101,017
[45] Date of Patent: Mar. 31, 1992

[54] ANTIBODIES FOR PROVIDING PROTECTION AGAINST P. VIVAX MALARIA INFECTION

[75] Inventors: Pablo Rubinstein, New Rochelle; Margaret Nichols, Mahopac, both of N.Y.

[73] Assignee: New York Blood Center, Inc., New York, N.Y.

[21] Appl. No.: 34,869

[22] Filed: Apr. 6, 1987

[51] Int. Cl.$^5$ .................. C07K 15/28; C12N 5/12
[52] U.S. Cl. .................. 530/388.22; 530/808; 530/809; 530/388.7; 530/387.2; 424/85.8; 435/70.2; 435/70.21; 435/172.2; 935/89; 935/95; 935/106; 935/107; 935/108
[58] Field of Search .................. 530/387, 808, 809; 435/18, 172.2, 70.2, 70.21; 424/85, 85.8; 935/89, 95, 106, 107, 108

[56] References Cited

U.S. PATENT DOCUMENTS

4,466,917  8/1984  Nussenzweig et al. ...... 4g340101/85

FOREIGN PATENT DOCUMENTS

8302896  9/1983  PCT Int'l Appl. .
8500975  3/1985  PCT Int'l Appl. .

OTHER PUBLICATIONS

Vernes et al., Am. J. Trop. Med. Hyg., 33(2), 1984, pp. 197–203.
Davies et al., Transfusion, 1979, vol. 9(5), p. 638.
Miller et al., Science 234, 1986, pp. 1349–1356.
Hadley et al., Science 223, 1984, pp. 597–599.
Moore et al., Nature 295, 1982, pp. 529–531.
Tharavanig, Southeast Asian J. Trop. Med. Pub. Health, 16, 1985, pp. 314–331.
Seuier et al., Clin. Chemistry 27(11), 1981, pp. 1797–1806.
Hollingdale et al., J. Immunol. 132, 1984, pp. 909–913.
A. C. Allison, "Polymorphism and Natural Selection in Human Populations", Cold-Spring Harbor Sympos., Quant. Biol., 29, 137 (1964).
M. J. Friedman, "Oxidant Damage Mediates Variant Red Cell Resistance to Malaria", Nature, 280, 245 (1979).
F. B. Livingston, "The Duffy Blood Groups, Vivax Malaria and Malaria Sections in Human Populations: Review", Human Biol., 56, 413 (1984).
L. H. Miller, H. J. Mason, D. F. Clyde and M. H. McGinnis, "The Resistance Factor to Plasmodium vivax in Blacks, The Duffy Blood Group Genotype (a–b–)", N. Engl. J. Med., 295, 302 (1976).
M. Hommel, "Antigenic Variation in Malaria Parasites", Immunology Today, 6, 28 (1985).
F. Zavala, A. Masuda, P. M. Graves, V. Nussenzweig and R. Nussenzweig, "Ubiquitey of the Repetitive Epitope of the CS Protein in Different Isolates of Human Malaria Parasites", J. Immunol., 135, 2790 (1985).
M. Hommel, P. H. David and L. D. Oligino, "Surface Alterations of Erythrocytes in Plasmodium falciparum Malaria. I. Antigenic Variation, Antigenic Diversity and the Role of the Spleen", J. Exp. Med., 157, 1137 (1983).
R. J. Howard, J. W. Barnwell and V. Kao, "Antigenic Variation in Plasmodium knowlesi Malaria: Identification of the Variant Antigen on Infected Erythrocytes", Proc. Natl. Acad. Sci., USA, 80, 4129 (1983).
R. S. Nussenzweig and V. Nussenzweig, "Development of Sporozoite Vaccines", Philos. Trans. R. Soc. Lond (Biol), 307, 117 (1984).
D. R. Spriggs, "The Malaria Sporozoite Vaccine", Parasitology's Brave New World, J. Infect. Dis., 152, 655 (1985).
H. C. Spencer, L. H. Miller, W. E. Collins et al., "The Duffy Blood Group and Resistance to Plasmodium vivax in Honduras", Am. J. Trop. Med. Hyg., 27, 664 (1978).

Primary Examiner—Garnette D. Draper
Attorney, Agent, or Firm—Sprung Horn Kramer & Woods

[57] ABSTRACT

A monoclonal antibody which identifies the human blood group Duffy (ab) is provided. Such monoclonal antibody blocks the penetration of P. vivax malaria parasite into human red blood cells by virtue of effective blocking of the target molecule of the P. vivax malaria parasite. Such monoclonal antibody has a combining site having the same stereochemistry as the ligand site on P. vivax, and elicits anti-idiotypic antibodies that react with the parasite.

3 Claims, No Drawings

ANTIBODIES FOR PROVIDING PROTECTION AGAINST P. VIVAX MALARIA INFECTION

BACKGROUND OF THE INVENTION

1. Field of the Invention

The present invention relates to a monoclonal antibody which identifies the human blood group Fyab of the Duffy system and the use of such monoclonal antibody to provide protection against P. vivax malaria infection by eliciting anti-idiotypic antibodies.

2. Background Information

Malaria is the most prevalent infectious disease of mankind. Its widespread geographic distribution together with the severe pathologic consequences of the infection make malaria a major medical and financial burden for many of the developing nations.

Its enormous prevalence and the clinical severity of is effects underlie its biological consequences as a natural selection agent. It has been shown that the frequency of the sickle-cell trait increases in areas of high malarial endemia, owing to the resistance of red cells from Ss heterozygous individuals against the successful multiplication of intracellular forms of the malarial parasite (A. C. Allison, "Polymorphism and Natural Selection in Human Populations", Cold Spring Harbor Sympos., Quant. Biol., 29, 137, (1964)). This is true in spite of the gene frequency decrease caused by the invariably early lethality of the homozygous form of sickle cell disease in nature (Allison, supra and M. J. Friedman, "Oxidant Damage Mediates Variant Red Cell Resistance to Malaria", Nature, 280, 245, (1979)).

There are several different kinds of malaria, one of which is caused by the parasite P. vivax, which attacks the red blood cells of susceptible individuals. A genetic trait of special interest with regard to P. vivax is the absence of antigens encoded by the blood group system called Duffy (F. B. Livingston, "The Duffy Blood Groups, Vivax Malaria and Malaria Sections in Human Populations: Review", Human Biol., 56, 413, (1984)). It has been shown that individuals whose red blood cells lack the product of the Duffy genes are not susceptible to the penetration of P. vivax owing to the fact that Duffy molecules serve as the receptor for the parasite (L. H. Miller, H. J. Mason, D. F. Clyde and M. H. McGinnis, "The Resistance Factor to *Plasmodium Vivax* in Blacks, The Duffy Blood Group Genotype (a-b-)", N. Engl. J. Med., 295, 302, (1976)).

The sporozoan protozoa of the genus Plasmodium are pigment-producing ameboid intracellular parasites of vertebrates, with one habitat in red blood cells and another in cells of other tissues. There are at least five species of *plasmodia* that may infect humans, one of which is *Plasmodium vivax* ("P. vivax").

Malarial parasites are transmitted from host to host by blood sucking females of several species of the genus *Anopheles*. It is in the mosquito that the sexual phase of the life cycle of P. vivax takes place leading to the production of sporozoites. After their introduction into a "new" host, these sporozoites reside in the parenchymal cells of the liver and multiply asexually causing the eventual rupture of the hepatic cells and the release of the asexual forms (merozoites) into the blood stream. There they actively penetrate into red blood cells in a nearly synchronous fashion and because the rate of growth and cell division of P. vivax merozoites is essentially identical, the infected erythrocytes simultaneously reach the stage of parasite load at which they break. This produces the typical cycles of fever every 48 hours, hence the name of Tertian malaria.

P. vivax infection may persist without treatment for as long as five years. P. vivax parasitemias are relatively low-grade, primarily because the parasites favor either young or old red blood cells, but not both.

Immunity to P. vivax is commonly only partial in nature, which allows the occurrence of super infections that evolve independently causing an overlap in the cycles of parasite release leading to the appearance of fever in shorter cycles. P. vivax exhibits considerable antigenic "diversity" and "variation", as do other malarial *Plasmodia* (M. Hommel, "Antigenic Variation in Malaria Parasites", Immunology Today, 6, 28, (1985)), although it has been recently shown that antigenic components of P. vivax sporozoites exist that are common to parasites from different isolates (F. Zavala, A. Masuda, P. M. Graves, V. Nussenzweig and R. Nussenzweig, "Ubiquity of the Repetitive Epitope of the CS Protein in Different Isolates of Human Malaria Parasites", J. Immunol., 135, 2790, (1985)).

"Diversity" refers to phenotypic differences between different isolates of the same species and is accompanied by isolate-specific differences in neoantigens appearing on the surface of infected erythrocytes (M. Hommel, P. H. David and L. D. Oligino, "Surface Alterations of Erythrocytes in *Plasmodium falciparum* Malaria. I. Antigenic Variation, Antigenic Diversity and the Role of the Spleen", J. Exp. Med., 157, 1137, (1983)). There is evidence that the weak and temporary immunity exhibited by malaria patients, formerly called "premunition", is due at least in part to these parasite-dependent erythrocitic antigens, which are also specific to the parasite strain in question (M. Hommel, "Antigenic Variation in Malaria parasites", supra). Diversity is an obvious obstacle in the quest for effective immunogenic methods for human vaccination.

Antigenic "variation" is a further difficulty which refers to the capacity of a single organism to express sequentially a variety of antigens of different specificities. Thus, the Plasmodium population parasitizing a given individual may "switch" the antigens it expresses. Variation has been very well studied in, among other species, experimental P. knowlesi malaria in monkeys. For example, two cloned variants were shown to cause the emergence of two red blood cell membrane proteins, each which differed immunologically and even in molecular size (R. J. Howard, J. W. Barnwell and V. Kao, "Antigenic Variation in *Plasmodium Knowlesi* Malaria: Identification of the Variant Antigen on Infected Erythrocytes", Proc. Natl. Acad. Sci., USA, 80, 4129, . (1983)).

In the context of these sources of antigenic differences between P. vivax isolates and their consequences with regard to vaccination, it is important that the merozoites of different strains of P. vivax share the same receptor for penetration into red blood cells, i.e., the Duffy molecule (Miller et al, N. Engl. J. Med., supra). In addition, regardless of its capacity to vary other antigenic molecules, the parasite recognition molecule, i.e., the molecule that binds to the Duffy molecule, must remain constant since it is the complementarity between it and the invariant receptor that allows the penetration of merozoites into erythrocytes and thus, the continuity of the infection. Changes in the ligand specificity of this molecule would result in the loss of the parasite's capacity to infect, since P. vivax merozoites appear to be unable to utilize other human red blood cell receptors for their penetration in vivo, as shown by the resistance of Duffy negative erythrocytes.

If antibodies against the parasite's ligand could be induced in susceptible individuals, such antibodies would recognize the ligand on the surface of the merozoites and would block its capacity to interact with red blood cells. They might also result in a reaction similar to that caused by antibodies to the so-called circunsporozoite (CS) protein, which terminates in the destruction of the sporozoites's viability in vitro as described by R. S. Nussenzweig and V. Nussenzweig, "Development of Sporozoite Vaccines", *Philos. Trans. R. Soc. Lond (Biol)*, 307, 117 (1984) and D. R. Spriggs, "The Malaria Sporozoite Vaccine: Parasitology's Brave New World", *J. Infect. Dis.*, 152, 655, (1985). It has not been possible, thus far, to identify, characterize and prepare such ligand molecules to allow a test of this hypothesis.

Blocking of *P. vivax* penetration by conventional antibodies of the Duffy blood group was described by H. C. Spencer, L. H. Miller, W. E. Collins et al, "The Duffy Blood Group and Resistance to *Plasmodium Vivax* in Honduras", *Am. J. Trop. Med. Hyg.*, 27, 664, (1978).

SUMMARY OF THE INVENTION

It is, accordingly, an object of the present invention to provide an improved way of combating malaria resulting from *P. vivax* by blocking the erthrocytic receptor of this parasite with an epitopic-specific monoclonal antibody.

Another object of the present invention is to prepare vaccines for the immunization of individuals susceptible to the so-called Benign Tertian Malaria caused by *P. vivax*, a parasite whose port of entry into red blood cells is the molecule that carried the blood group antigens of the Duffy system, which is thus referred to as its receptor. Conversely, *P. vivax* depends on the expression on its surface of a *specific* molecule (referred to as the ligand), stereochemically complementary to the receptor for its binding to and/or, subsequent penetration into the erythrocyte. This ligand is thoroughly inhibited in its binding to the receptor (in the specific case of *P. vivax*, the receptor molecule corresponds to the Duffy blood group antigen) by the monoclonal antibody which is the subject of the present invention and which possesses the same sterochemical specificity. Thus, immunization with this monoclonal antibody as a vaccine will elicit an immune response to its combining site, termed an anti-idiotypic response, resulting in antibodies which will also recognize the immunologically identical epitope on the ligand and hence will protect the host against the erythrocytic forms (merozoites) of *P. vivax.*

The present invention concerns the use of monoclonal anti-receptor antibodies immunochemically specific for the epitope used by *P. vivax* and for those used by other parasitic organisms, including viruses and bacteria, to penetrate into host cells. These monoclonal antibodies are used according to the present invention, to generate or elicit the corresponding anti-idiotypic antibodies which by virtue of their specificity for the parasite's ligand molecule are useful in the serodiagnosis and treatment of established infection.

In accordance with another aspect of the invention, the antibodies according to the invention can be used to produce anti-idiotypic antibodies outside the human body and such anti-idiotypic antibodies can be used to isolate the particular molecules of *P. vivax* which are responsible for red blood cell penetration by *P. vivax.* Those molecules will combine with the anti-idiotypic antibodies, the complexes isolated and then broken apart to liberate the particular parasitic molecules. Those molecules can thereafter be used in various ways to generate an immunologically adequate vaccine that results in the production of antibodies to such particular molecules.

The present invention also concerns a general method for producing immunity against an infectious microorganism based on the stereochemical complementarity between the ligand molecule on the microorganism and its receptor in the host's cell. This complementarity is used according to the present invention to generate antibodies against the ligand by immunizing with monoclonal antibodies against the ligand-binding region of the receptor molecule. Such monoclonal anti-receptor antibodies, which react with the exact area of binding of the ligand molecule of the parasitic organism, bring about protective immunity because they elicit anti-idiotypic antibodies that react with the stereochemically equivalent region of the ligand.

Fundamental to the herein described invention is the fact that there is obtained a monoclonal antibody which identifies the human blood group antigen $Fy^{ab}$ of the Duffy system. As concerns the present invention, more specifically, there is obtained a monoclonal antibody that blocks penetration of *P. vivax* malaria parasite into human red blood cells by virtue of effectively blocking the site on the Duffy-erythrocytic molecule used as a target by the *P. vivax* malaria parasite. There is provided according to the invention a monoclonal antibody the combining site of which has the same stereochemical configuration as the ligand site on the *P. vivax* malaria parasite. This antibody is prepared by standard methods. Specifically, red blood cells from a donor carrying the Duffy (ab) group are injected into an animal such as a mouse, the animal's spleen is excised and the spleen cells separated, fused with myeloma cells to produce a hybridoma and the hybridoma cloned in the wells of tissue-culture microtiter trays. The antibodies produced by the cells in various wells are tested with blood cells of the four different Duffy kinds. viz., Fy a+, b+, (ab)+

Fy a−, b+, (ab)+

Fy a+, b−, (ab)+

Fy a−, b−, (ab)−

Those which selectively react with all the first three, but not the fourth, are potentially useful in the practice of the invention. The selected cloned hybridomas produce as large quantities of suitable monoclonal antibodies as desired.

Stated otherwise, the present invention concerns a monoclonal antibody that can react with all human red blood cell samples that contain either or both blood group antigens $Fy^a$ and $Fy^b$ and does not react with any other human blood samples. This specificity is similar to the well known blood group Fy3, but differs from it in that the $Fy^{(ab)}$ epitope is sensitive to degradation by proteolytic enzymes, such as trypsin, papain and ficin.

Such antibodies can be passively utilized for blocking a patient's red blood cells so that the penetration of *P. vivax* merozoites is efficiently impeded or can be used as antigens injected into mice to produce anti-antibodies, i.e., anti-idiotypic antibodies. Among such secondary antibodies, some will have binding sites immunologically complementary to and reactive against the ligand molecule of *P. vivax* and will therefore interfere with its penetration into the red blood cells. The anti-Fy$^{(ab)}$ monoclonal antibody used in susceptible humans will lead to the formation of similar human anti-idiotypic antibodies, which also recognize the red blood cell binding ligand on *P. vivax* merozoites, and which will provide protection against *P. vivax* penetration.

In other words, anti-Fy$^{(ab)}$ may be used as follows:

(a) as passive blockers of the receptors, "hiding" them from the parasite's ligand in order to prevent the parasite from penetrating into red blood cells, or (b) to induce anti-idiotypic antibodies, either in susceptible humans (which renders anti-Fy$^{(ab)}$ a vaccine) or in an animal which would lead to the production of hyperimmune globulins against the parasite's invariant red blood cell binding site. Such foreign hyperimmune globulins may be used in passive immunotherapy, while anti-idiotypic antibodies induced in a susceptible host provide active immunity against the ligand.

In the present invention, the ligand molecule of *P. vivax* is by-passed for immunization purposes, by using instead antibody molecules possessing the identical specificity, i.e., which are immunochemically specific for the same epitope on the red cell receptor (Duffy) molecule. In the present invention, there is prepared such antibodies in the form of murine monoclonal antibodies having the capacity to inhibit the penetration of *P. vivax* into Duffy-positive red blood cells. This inhibition is similar in character and specificity, but stronger in quantitative terms, than that reported for conventional antibodies of the Duffy blood group specificity (H. L. Spencer et al, supra). In addition, these antibodies precipitate, from solubilized erythrocytic membranes, a 45kD glycoprotein bearing the ; Duffy blood groups.

The monoclonal antibodies of the present invention when injected into immunologically competent hosts result in the formation of anti-idiotypic antibodies, i.e., antibodies that recognize the specific combining site (idiotype) of the immunizing anti-Duffy monoclonal antibody. Given that the combining sites of both this anti-Duffy antibody and the ligand molecule of *P. vivax* recognize one and the same receptor epitope, antibodies reacting against the first should, by necessity, also recognize and react against the second.

Immunizations can be performed by injecting immunoglobulin molecules purified from the monoclonal antibody into host animals. The antibody response of the immune animals will contain anti-idiotypic antibodies which, according the present invention, will react not only with the anti-Duffy molecules, but also with the ligand molecule on the surface of the parasite. These anti-idiotypic antibodies would be protective, if their hosts were otherwise susceptible to *P. vivax*, by virtue of their ability to interact immunologically with the parasite. Thus, the monoclonal antibody against the receptor molecule for *P. vivax* could serve as an immunogenic vaccine for the protection of susceptible individuals. In addition, extraction of the ligand from merozoites by using anti-idiotypic antibodies will permit the preparation of further immunogens from the same ligand molecule, as well as a detailed understanding of the molecular events of merozoite penetration. Finally, by their specificity against the indispensible (and most likely invariant) ligand molecule, these antibodies would be effective regardless of the parasite's strain.

DETAILED DESCRIPTION OF THE INVENTION

The present invention relates to a novel method of immunizing susceptible human individuals against *P. vivax* merozoites and is based on the development of a mouse monoclonal antibody recognizing the parasite-binding region of the Duffy molecule, which is the human receptor for *P. vivax* merozoites. Because of its blood group specificity, the corresponding epitope . has been designated Fy(ab).

Since the monoclonal anti-Fy$^{(ab)}$ antibody and the ligand structures on the parasite's red cell-binding molecule recognize the same epitope, antibodies specific for the combining site on the anti-Fy$^{(ab)}$ antibody (anti-idiotypic antibodies), can be elicited, which will react with the parasite's ligand. Susceptible individuals who make these anti-idiotypic antibodies will be protected against *P. vivax* merozoites because (a) they block the ability of the parasite to recognize the erythrocytic receptor and (b) they may induce the lysis or inactivation of the Plasmodium cell by fixing complement.

There are three procedures for immortalizing antibody-producing B-cells in current use. These are: (1) the conventional fusion to a selectable myeloma cell line, as originally described by Kohler and Milstein, Nature, 256, 495–497, (1975), (2) transformation and immortalization by Epstein-Barr virus (on human B cells) as reported first by M. Steinitz, G. Klein, S. Koskimies, and Makela, Nature, 269, 420–422, (1977) and, (3) a combination of both techniques. However, it may be anticipated that other, more effective techniques may be used to yield antibody-producing cell lines, including transfection with genetically engineered constructs including the rearranged immunoglobulin genes coupled with efficient promotors.

One method of preparing the hybridomas according to the present invention comprises the following steps:

(a) Immunizing mice with human red cells from a donor having the Duffy (ab) blood group antigen. While BALB/cJ mice are preferred, it is contemplated that other mouse or rat strains could be used.

(b) Removing the spleens and/or lymph-nodes from the immunized animals and making a spleen or lymph-node cell suspension in an appropriate medium.

(c) Fusing the suspended spleen or lymph-node cells with mouse or rat myeloma cells from suitable cell lines by the use of any appropriate fusion promotor. The usually preferred ratio is about four nucleated spleen cells to each myeloma cell. Several mouse and rat myeloma cell lines are known and available, generally from members of the academic community or various deposit banks, such as the Salk Institute Cell Distribution Center, La Jolla, CA. Most commonly used are the 8-azaguanine resistant cell lines, which lack the enzyme hypoxanthine-guanine phophoribosyl-transferase. It is also generally preferred that the myeloma cell line used be of the so-called "non-secreting" type, i.e., one that does not itself produce any antibody, although secreting types may be used. While the commonly used fusion promotor is polyethylene glycol having an average molecular weight from about 1000 to about 4000 (commercially available as PEG 1000 to PEG 4000, etc.), other fusion promoters known in the art may be employed, including other chemicals, viruses and physical agents, such as electric discharges through the suspension.

(d) Diluting the mixtures of unfused spleen or lymph-node cells, unfused myeloma cells and fused cells and culturing these mixtures in a selective medium, which will not support the unfused myeloma cells for a time sufficient to result in the death of the unfused cells (about 14–16 days). The medium is one which will not support the enzyme-deficient unfused myeloma cell line. Hence, these myeloma cells perish. The unfused spleen or lymph-node cells are non-malignant, and thus survive only through a finite number of generations. Thus, after a certain period of time (about 14 to 16 days) these unfused normal cells are essentially all dead. The fused, hybrid cells, on the other hand, continue to reproduce because they possess both the malignant quality of the myeloma parent and the ability to survive in the selective medium of the normal cell parent.

(e) Selecting by limiting dilution, i.e., one in which the volume of diluent is statistically calculated to isolate a certain number of cells (e.g., 0.3 to 1) in a given volume of suspension deposited in each separate container (e.g., each well of a microtiter plate), or by alternative methods, such as by culturing in soft agars, and cloning hybridomas that produce and secrete the desired antibody of the desired blood group specificity, i.e., reacting with all human cells but $Fy^{(a-b-)}$ ones.

Once the desired hybridoma has been selected and cloned, the resultant antibody may be produced in one of two ways. The purest monoclonal antibody is produced by in vitro culturing of the desired hybridoma in a suitable medium for a suitable length of time, followed by recovery of the desired antibody from the supernatant. The suitable medium and suitable length of culturing time are determined empirically. This in vitro technique produces monoclonal antibody, free from other antihuman immunoglobulin. There is a small amount of other immunoglobulin present since the medium contains xenogeneic serum (e.g., fetal calf serum). This type of gamma globulin, however, is no consequence since its immunoglobulins content is very low and its lack of binding to human cells is routinely established for each batch before using it for this purpose. This in vitro method yields a concentration of monoclonal antibody usually in the 5 to 20 μg/ml range, which may be insufficient for some purposes.

To produce a much greater concentration of slightly less pure monoclonal antibody, the desired hybridoma may be injected into mice or rats syngeneic or semi-syngeneic with the strain of the myeloma, to which the spleen or lymph-node donor also belongs. The hybridoma will cause formation of antibody-producing tumors, which will result in a high concentration of the desired antibody (about 5 to 20 mg/ml) in the bloodstream and peritoneal exudate (ascites) of the host animal. To increase the volume of ascites, the hosts are pretreated with intra-peritoneal injections of irritants (e.g., pristane, Freund's adjuvant, silica gel, etc.).

Although the monoclonal antibody concentration is higher in ascitic fluids, normal immunoglobulins from the host animal containing species antibody are also present there.

However, the monoclonal antibody in ascitic fluids is typically of high titer and contains an extremely high ratio of specific to non-specific immunoglobulin.

When used for vaccination, the novel immunoglobulins of the present invention can be administered, with adjuvants, if warranted, by any medically acceptable route including the following: oral, intravenous, rectal, subcutaneous, intradermal or intramuscular.

The monoclonal antibody according to the invention has the following characteristics and properties:

(1) The monoclonal antibody of the present invention can be used as the immunogenic agent in a vaccine and can be produced in virtually limitless quantity.

(2) The region of the antibody molecule that bears the immunogenic moiety (idiotype) is located in the variable region which may be further purified in order to avoid the undesired immunogenicity of the constant region of the molecule.

(3) If desired, the antigen combining region of the monoclonal antibody can be transferred to a carrier molecule devoid of additional immunogenic properties for human subjects. This may be done by a number of methods that are equivalent in this regard, such as, by chemically binding the Fab fragment of the antibody molecule to an Fc fragment derived from human immunoglobulin or by genetically engineering an appropriate hybrid molecule using the necessary portion of the rearranged immunoglobulin heavy and light chain genes from the monoclonal-producing hybridoma cell line into human immunoglobulin genes from which the equivalent regions have been excised. Alternatively, the idiotype-bearing portions of the protein (or the DNA fragments encoding them) may be attached to other immunogenic molecules or particles (or to their respective genetic determinants in the case of the DNA fragments encoding the idiotypes).

(4) The monoclonal antibody of the present invention can precipitate from red cells, and thus may be used to chemically isolate, the human receptor for *P. vivax* which will permit the precise characterization of the ligand region of the receptor molecule. In turn, the purified red blood cell receptor, or synthetic molecules fashioned after it, may be used for binding to and isolating the parasite's specific recognition molecule. The purified ligand molecules from the merozoite could then be characterized and used as "blue-prints" for the preparation of synthetic peptides with protective immunogenic properties (5) The monoclonal antibody of the present invention can be used to prepare anti-idiotypic monoclonal antibodies in mice. Those anti-idiotypic antibodies that additionally react with the combining site of *P. vivax* merozoites can be used as affinity probes, to isolate the ligand as was described in (4) above for the receptor on red blood cells and with the same objectives.

(6) The monoclonal antibody of the present invention and the anti-idiotypic antibody of the present invention can be used in the immunodiagnosis of *P. vivax* infection. Thus, the presence of *P. vivax* antigen in serum or other fluid may be detected and its concentration measured by its interference with the binding of the monoclonal anti-Duffy to either the Duffy molecule or to its monoclonal anti-idiotypic antibody. Since the parasite's ligand and the anti-Duffy antibody will react with the same combining site both on the Duffy molecule and in the monoclonal anti-idiotypic immunoglobulin, a simple competition assay can be designed using either enzyme-linked or radiolabeled reagents, or other labeling reagents.

(7) The use of monoclonal antibodies to the receptor molecule to induce anti-idiotypic responses which protect against parasites can be extended to organisms other than *P. vivax*. For example, it is now believed that the receptor for *P. falciparum* merozoites is located in the glycophorin A and/or glycophorin B molecules (L. Perrin, A. Perez and C. Chizzolini, "Malaria: Immunity, Vaccination and Immunodiagnosis", *Experientia*, 40, 1343, (1984)). Several monoclonal antibodies have been developed that react with epitopes on these two molecules (M. Nichols, "Monoclonal Antibodies to Human Blood Groups. A Method and Its Application", PhD Thesis, Cornell University, (1985); M. Nichols, R. E. Rosenfield and P. Rubinstein, "Two Blood Group M Epitopes Disclosed by Monoclonal Antibodies", *Vox. Sang.*, 49, 138, (1985)) and further monoclonals may be prepared with this purpose. Other pathogens which penetrate human cells through defined receptors are known, e.g., the HTLV-III/LAV and Epstein-Barr viruses and similar approaches to specific vaccine development are contemplated.

(8) The monoclonal anti-Duffy antibodies may be used directly in vivo to block the red cell receptors for the parasite. This might be useful in the management of patients with particularly severe attacks of *P. vivax* malaria, in whom the level of parasitemia may be very high. In the same type of patients, but not simultaneously, passively administered anti-idiotypic antibodies may be useful by directly binding to and destroying the parasites.

The present invention also provides a method for the detection of the presence of *P. vivax* infection in a patient. The method employs insolubilized monoclonal antibody which identifies the human blood group $Fy^{(ab)}$ of the Duffy system and labeled, e.g., radiolabeled or enzyme labeled, monoclonal anti-idiotypic antibody to the aforesaid monoclonal antibody. Soluble *P. vivax* in the test sample will interfere with the binding to the insolublized monoclonal antibody of the labeled monoclonal anti-idiotypic antibody and will thus decrease the amount of the detectable label, e.g., the radioactivity or the enzyme, bound by the insolublized antibody.

Non-limiting examples of supports for affinity-separation of antibodies, including monoclonals, include the following: activated sepharose, activated cellulose and activated sephadex. "Activated" refers to the creation, on the insoluble material, of reactive chemical groups that will form covalent linkages with the antibody molecules when incubated together under appropriate conditions. Typically, reactive groups are introduced into the insoluble substrate by the action of cyanogen bromide (CNBr) at high pH.

The invention will be further described with reference to the following non-limiting examples:

EXAMPLE 1

Preparation and Identification of a Murine Monoclonal Antibody Which Specifically Recognizes the Receptor Molecule for *P. vivax*, Taking Advantage of the Presence on the Same Molecule of the Antigens of the Duffy Blood Group Using the method of G. Kohler and C. Milstein, *Nature* 256, 495–496, (1975), a BALB/c mouse was immunized with washed human red cells of the $Fy^{(a+b+)}$ type by six weekly intraperitoneal administration of $10^7$ erythrocytes each. The spleen of the mouse was then removed and a cell suspension prepared in tissue culture medium (RPMI-1640 with additional glutamine, 5mM). The spleen cell suspension was mixed with a suspension of the mouse myeloma cell line P3/NSO-Ag4-1 (NS-0) (obtained from the ATCC) which, being deficient in the enzyme hypoxanthine-guanine phosphoribosyltransferase (HGPRT), will not grow in tissue culture media containing hypoxanthine, aminopterin and thymidine (HAT media).

The mixture contained four spleen cells to one myeloma cell. Fusion was promoted by the addition of polyethylene glycol (PEG) of an average molecular weight of 2000. After fusion, the cells were washed free of PEG, resuspended in HAT medium and allowed to grow to a density of $10^6$ live cells per ml and aliquots of 0.1 ml added to the wells of a 24-well tray containing feeder cells (from BALB/c thymus).

Partial changes of culture medium were performed at 3, 5 and 7 days and the supernatants removed 14 days postfusion and tested for the presence of antibodies that bind to human red cells. Since the process was conducted in the presence of HAT, essentially non-fused myeloma cells were dead at this time, which prevented them from possibly overgrowing the fused (hybrid) ones.

The unfused spleen cells were also dead because of their very limited capacity to grow ex vivo in this tissue culture medium. The hybrid cells grew and multiplied because the normal spleen cells contributed the enzyme HGPRT and the myelomatous cells for the capacity for indefinite proliferation. The supernatants from the wells containing colonies of hybrid cells were assayed on a panel of cells including the major Duffy genotypes: $Fy^{(a+b-)}$, $Fy^{(a-b+)}$ and $Fy^{(a-b-)}$. One well was found to contain antibodies that bound to the first two types and not the third. The cellular contents of that well were then recovered and suspended to a concentration of 3 cells per ml.

Aliquots of 0.1 ml were then added to fresh wells, so that on the average only one of every three wells received a cell and, thus, the colonies that resulted from the growth of this very diluted suspension are likely to be true "clones", i.e., descendents from a single progenitor. When the colonies attained a size of $10^2$ cells their supernatants were again screened for the presence of Duffy antibodies and the 10 most strongly positive ones allowed to expand to a number of $10^5$ to $10^6$. Dilution of these cell suspensions to a concentration of 3 cells/ml and plating volumes of 0.1 ml as before resulted in the growth of doubly-cloned hybrid, antibody- producing cell lines. One of these, designated K6F4, ATCC No. 9332, deposited on February 25, 1987 with the American Type Culture Collection, Rockville Maryland, was grown to a total cell number of $10^9$, and aliquots of $10^7$ cells were frozen in liquid nitrogen to ensure the continuity of this cell line.

The concentration of monoclonal antibody at the time of maturity of a culture flask is $20\pm5$ μg/ml. The cloned hybridoma also grows in vivo in mice of the BALB/c strain or of its first generation (F1) hybrids. This growth is in the form of malignant myelomatous tumors. When live hybridoma cells are injected up into susceptible animals, they secrete high concentrations of antibody into the peritoneal spaces. "Priming" the animals with irritants such as incomplete Freund's adjuvant or Pristane injected into the peritoneum, before grafting the hybridoms, results in the formation of large volumes of ascites containing antibody in concentrations higher than 5 mg/ml.

EXAMPLE 2

Serological Characterization and Immunogenetic Specificity

The K6/F4 monoclonal antibody from Example 1 was tested for reactivity on a large panel of otherwise unselected human red cells, and others that include rare blood-types, with particular emphasis on the different Duffy blood groups. These tests were performed with the antiglobulin technique using rabbit anti-mouse gamma-globulin antisera, previously adsorbed with washed human red cells to remove contaminating anti-human (species) antibodies.

The monoclonal antibody was also tested against a panel of red blood cells from individuals of several non-human primate species, in parallel with eluates of conventional human antibodies of known Duffy blood group specificity.

EXAMPLE 2a

Tests on Human Red Cells

Highly selected red cells panels were prepared locally by choosing donors of informative blood types or obtained commercially. A local panel was first used to confirm the initial screening results that indicated the antibody to be non-reactive with $Fy^{(a-b-)}$ red blood cells. The regular local panel contained three $Fy^{(a-b-)}$ samples which differ extensively in their phenotypes from other blood groups. All three were negative, as were the $Fy^{(a-b-)}$ cells in three Accugenics panels, while all others were strongly reactive. "Rare" cells of the following types were positive: Ge(−); Vel(−1, −2); $Jk^{(a-b-)}$; Oh(Bombay); Lan(−) Tj(a−); Rh null, (two examples); U(−); Hy(−)/$Jo^a$(−0; $Jr^a$(−); $Wr^b$(−); K−2 and $Lu^{(a-b-)}$ (many examples) including both dominant and recessive forms; Fyx/Fyx; and two examples of the very rare $Fy^{(a-b-)}$ phenotype from white donors.

In addition, several hundred unselected blood donor samples were tested. All of which were $Fy^{(a-b-)}$, but no others, were negative.

Thus, the serological specificity of K6/F4 is similar to that of the Fy3 antigen, which is present whenever either of the $Fy^a$ or $Fy^b$ genes are expressed. It is different from Fy5, a similar specificity which is, however, also absent from Rh null cells. The K6/F4 monoclonal antibody reacts well with Rh null cells.

Interestingly, however, the antigenic epitope recognized by K6/F4 differs from that of conventional Fy3 in its susceptibility to enzyme treatment.

Human red blood cells of the four relevant phenotypes, $Fy^{(a+b-)}$, $Fy^{(a-b+)}$, $Fy^{(a+b+)}$ and $Fy^{(a-b-)}$ were treated under standard conditions (American Association of Blood Banks, Technical Manual, 9th Edition, 1985) with the enzymes Ficin, Papain, Bromelin, Pronase, Neuraminidase and Trypsin. Aliquots were then exposed to (human) anti-$Fy^a$, anti-$Fy^b$, anti-Fy3 and K6/F4 supernatant. All these enzymes, with the exception of Neuraminidase, abolished the reactivity of the monoclonal reagent, while only Pronase destroyed that of the human anti-Fy3. As is already known, Neuraminidase did not affect either $Fy^a$ or $Fy^b$; Trypsin destroyed $Fy^b$, but not $Fy^a$; Bromelin is similar to Trypsin and both Ficin and Papain destroyed both antigenic specificities.

Thus, the specificity recognized by K6/F4 is conveyed by an epitope distinct at the molecular level, although very closely associated with $Fy^a$, $Fy^b$ and Fy3. This epitope was designated $Fy^{(ab)}$.

EXAMPLE 2b

Tests on Non-human Primate Erythrocytes

The tests of Example 2b were conducted as a further check on the specificity of the monoclonal anti-Duffy. These tests were performed in parallel with the conventional human reagents, using eluates prepared from positive human cells in order to avoid the species antibodies contained in most human sera (M. Palatnik and A. W. Rowe, "Duffy and Duffy-Related Human Antigens in Primates", *J. Human Evolution*, 13, 173, (1984)).

The reactivity was as listed below:

|  | Monoclonal K6/F4 | $Fy^a$ | $Fy^b$ | Fy3 |
|---|---|---|---|---|
| Gorilla (*Gorilla gorilla*) | + | − | + (weak) | + |
| Chimpanzee (*Pan troglodytes*) | + + + + | − | + | + |
| Gibbon (*Hylobates agilis*) | + | − | + | + |
| Rhesus (*Macaca Mulatta*) | − | − | − | + (weak) |
| Baboon (*Papio sp*) | − | − | NT | + |
| Squirrel (*Saimiri sciureus*) | + + + + | − | − | NT |
| Capuchin (*Cebus apella*) | − | − | − | NT |
| Dourocoli (*Aotus trivirgatus*) | + + + + | − | − | + |

NT = not tested
− = negative test
+ = positive (weak) test
+ + + + = positive (strong) test The above results are significant to the objectives of the present invention, because the reactivity with the monoclonal K6/F4 reagent closely correlates with the susceptibility of cells to the penetration of P. vivax merozoites, as described below:

EXAMPLE 3

Capacity of the Monoclonal Anti-Fy(ab) Antibody to Block the Penetration of P. Vivax Merozoites into Erythrocytes The techniques used in Example 3 to ascertain penetration of *P. vivax* merozoite were adapted from those described in L. H. Miller, S. J. Mason, J. A. Dvorak, T. Shiroishi and M. H. McGinnis, "Erythrocyte Receptors for Malarial Merozoites and the Duffy Blood Group System", *Human Blood Groups*, 5th International Convocation on Immunology, Buffalo, NY, 1976, Basel Karger, pp. 394–400, 1977. Standard numbers of merozoites are incubated with standard numbers of erythrocytes. In parallel wells, red cells or primates of different species are exposed to *P. vivax* in the presence of either monoclonal anti-$Fy^{(ab)}$ antibodies or monoclonal anti-Rh29 or anti-Kl4 as controls. Anti-Rh29 and anti-Kl4 antibodies are reactive with essentially all human and most primate red blood cells, but their antigenic epitopes are unrelated to Duffy. A third well for each erythrocyte donor contains only tissue culture medium instead of monoclonal antibodies. The two latter, control, wells allow the determination of the proportion of red cells that are "normally" penetrated by the parasite under these conditions. Thus, comparison between this proportion and that in the well containing the K6/F4 monoclonal antibody permits estimation of its inhibitory effect This inhibition is well over 90% for human red cells and somewhat lower for Aotus and Saimiri erythrocytes. The inhibitory effects are reproducible and roughly parallel the serological reactivity of the red blood cell-monoclonal K6/F4 antibody combinations, as described above, even in the cases of primates that are negative for the conventional Duffy antigens, $Fy^a$ and $Fy^b$ (Saimiri and Dourocoli).

EXAMPLE 4

Chemical Studies

The anti-Fy6 monoclonal antibody was tested for its capacity to immunoprecipitate the 42-45kD glycoprotein from human red blood cells that is also the binding site for alloantibodies to the Duffy blood group (T. S. Hadley, et al supra Identification of an Erythrocyte Component Carrying the Duffy Blood Group $Fy^a$ Antigen, *Science*, 223, 597-599 (1983)). In fact, red blood cell membrane proteins, separated by SDS-PAGE and blotted onto nitrocellulose filters were exposed to labeled monoclonal antibody molecules and a single band of the appropriate molecular size and overall chemical characteristics was obtained.

EXAMPLE 5

Preparation of Monoclonal Anti-idiotypic Antibodies

All antibody molecules are, at the same time, antigens since their ability to function as antibodies, i.e., to bind to antigen, depends on a special stereochemical configuration which is specific for each antibody and is called an "idiotype". A monoclonal antibody immunoglobulin is constituted of exactly identical molecules, each having the same specific combining site, which, being complementary to the respective antigen, becomes antigenic for the antibody-producing host and to other animals of the same strain. In other words, the idiotype of an antibody leads to the production of anti-idiotypic antibodies. This antigenic property can thus be used to elicit such anti-idiotypic antibodies by injecting naive hosts with purified monoclonal antibodies produced in animals of the same inbred strain.

This is accomplished by first purifying the original monoclonal antibody (designated Ab1) by affinity chromatography, emulsifying it in complete Freund's adjuvant and injecting this emulsion into the peritoneum and under the skin in multiple sites of BALb/c mice. A second, identical injection is given two weeks later. Subsequent injections require the use of incomplete Freund's adjuvant Although the schedule of these injections and the quantities of immunoglobulin injected are empirical and different procedures have been reported to be successful, in this case two further injections in complete Freund's are given two weeks apart and following the initial two injections in complete Freund's adjuvant by two weeks. The recipient mice are rested for two months followed by two bi-weekly injections of F6/K4 (Ab1). One week later, the spleens are removed and fused with NSO myeloma cells. Hybridomas are grown as described elsewhere in this application and screening is performed by competitive inhibition of Ab1 binding to human red cells of appropriate Duffy type (i.e., other than $Fy^{(a-b-)}$). This inhibition test consists of adding the supernatants of hybridomas putatively producing anti-idiotypic antibodies (Ab2) to a dilution of F6/K4 and allowing the mixture to react with Fy(ab) cells. The presence of Ab2 inhibits that reaction. Confirmation of the specificity of presumptive anti-idiotypic antibody produced by the hybridomas is conducted by measuring its binding to red blood cells (there should be none) and the inhibition of monoclonal antibodies of the unrelated specificities: Rh29, K2, Kl4, M, N, B and $Wr^b$ (again there should be none). All these control tests being negative, the cells making the anti-anti-$Fy^{(ab)}$ antibody are cloned by limiting dilution.

These Ab2-producing clones (anti-anti-$Fy^{(ab)}$) are then expanded and used to produce large amounts of supernatant and ascitic fluids. Ab2 binding to, and inhibition of the red cell penetration by, *P. vivax* merozoites in subsequent experiments demonstrates that the epitope recognized by the anti-$Fy^{(ab)}$ monoclonal antibody is indeed the site used by *P. vivax* since the parasite shares the binding structure of the monoclonal antibody.

It will be understood that the specification and example are illustrative, but not limitative of the present invention and that other embodiments within the spirit and scope of the invention will suggest themselves to those skilled in the art.

What is claimed is:

1. A hybridoma cell line which secretes a monoclonal antibody which identifies a distinct antigen of the Duffy system, $Fy^{(ab)}$, the hybridoma being identified as ATCC No. HB 9332.

2. A monoclonal antibody secreted by hybridoma ATCC No. HB 9332.

3. A monoclonal antibody which identifies a distinct antigen of the Duffy system, $Fy^{(ab)}$, which has a combining site having the same sterochemical configuration as the ligand site on the P. vivax malaria parasite and which blocks penetration of *P. vivax* merozoite malaria parasite into human red blood cells by virtue of effectively blocking the erthrocytic molecule used as a target by the *P. vivax* malaria parasite.

* * * * *

UNITED STATES PATENT AND TRADEMARK OFFICE
CERTIFICATE OF CORRECTION

PATENT NO. : 5,101,017
DATED : March 31 1992
INVENTOR(S) : Rubinstein et al.

It is certified that error appears in the above-identified patent and that said Letters Patent is hereby corrected as shown below:

Title Page    U.S. PATENT DOCUMENTS: After " 4,466,917, 8/1984, Nussenzweig et al. ..... " delete " 4g340101/85 " and substitute -- 260/112 --

Signed and Sealed this

Second Day of November, 1993

Attest:

BRUCE LEHMAN

Attesting Officer    Commissioner of Patents and Trademarks